United States Patent [19]

Maulding

[11] Patent Number: 4,757,146

[45] Date of Patent: Jul. 12, 1988

[54] METHOD FOR THE PREPARATION OF QUINOLINE-2,3-DICARBOXYLIC ACID

[75] Inventor: Donald R. Maulding, Somerville, N.J.

[73] Assignee: American Cyanamid Company, Stamford, Conn.

[21] Appl. No.: 902,273

[22] Filed: Aug. 29, 1986

[51] Int. Cl.$^4$ .............................................. C07D 215/54
[52] U.S. Cl. ...................................... 546/170; 546/84; 548/546
[58] Field of Search ................... 546/170, 84; 548/546

[56] References Cited

U.S. PATENT DOCUMENTS 4,459,409  7/1984  Ladner ............................... 546/170

Primary Examiner—Richard L. Raymond
Assistant Examiner—D. B. Springer
Attorney, Agent, or Firm—Estelle J. Tsevdos

[57] ABSTRACT

The present invention relates to novel methods for the preparation of quinoline-2,3-dicarboxylic acid, useful for the preparation of the highly effective 2-(2-imidazolin-2-yl)quinoline-3-carboxylic acid herbicidal agents.

7 Claims, No Drawings

METHOD FOR THE PREPARATION OF QUINOLINE-2,3-DICARBOXYLIC ACID

BACKGROUND OF THE INVENTION

The present invention relates to novel methods for preparing quinoline-2,3-dicarboxylic acids. These acids are useful intermediates in the preparation of herbicidal pyridine and quinoline imidazolinone herbicidal compounds.

The herbicidal pyridine and quinoline imidazolinone compounds prepared from the present compounds include 2-(4-isopropyl-4-methyl-5-oxo-2-imidazolin-2-yl)quinoline-3-carboxylic acid, esters and salts thereof and are disclosed in European Patent Application No. 0,041,623, incorporated herein by reference. These herbicidal imidazolinyl quinolinecarboxylic acids may be prepared by the procedure described in U.S. Pat. No. 4,518,780 (incorporated herein by reference) by cyclization, under basic conditions, with an appropriately substituted 2-carbamoyl quinoline-3-carboxylic acid, that, in turn, is prepared by the reaction of a substituted quinoline-2,3-dicarboxylic acid anhydride and appropriately substituted aminocarboxamide or aminothiocarboxamide. Quinoline-2,3-dicarboxylic acid anhydrides are readily prepared from the diacids by procedures well known in the art. However, the diacids themselves are not readily available.

Existing procedures for preparing esters of quinoline-2,3-dicarboxylic acid include the Friedlander reaction of 2-aminobenzaldehyde with diethyloxalacetate, as described by L. Hozer and S. von Niementowski, *J. Prakt. Chem.*, 116(2): 43 (1927) and P. Caluwe, *Tetranedron*, 36: 2359 (1984), and the ozonolysis of acridine as described by A. Godard, G. Zueguiner, P. Pastour in *Bull. Soc. Chim. France*, 906 (1971). These methods are not suitable for the manufacture of large quantities of materials because of difficulty in preparing and storing 2-aminobenzaldehyde. 2-aminobenzaldehyde is not only unstable, but there are limited supplies of acridine in order to prepare said 2-aminobenzaldehyde. Therefore, other routes have been preferred.

On such other synthesis is disclosed in pending application for U.S. Letters Patent of Robert Doehner, Ser. No. 698,192 filed Feb. 4, 1985 (incorporated herein by reference) which describes a method for the preparation of quinoline-2,3-dicarboxylic acid and esters thereof by reacting a beta-anilino-alpha,beta-unsaturated ester with an immonium salt (commonly called a Vilsmeir reagent). The beta-anilino-alpha,beta-unsaturated esters are obtained by the reaction of appropriately substituted anilines with ketoesters or dialkyl acetylene dicarboxylates.

Unfortunately, the availability of ketoesters and dialkyl acetylene dicarboxylates, such as diethyloxalacetate and diethyl acetylenedicarboxylate is limited, thereby restricting the quantities of anilinofumarate, a precursor to quinoline-2,3-dicarboxylic acid.

Co-pending applications for U.S. Letters Patent of D. Maulding, Ser. No. 902,275 and 902,274, filed concurrently herewith and incorporated herein by reference, provide effective methods for the preparation of anilinofumarate by reacting dichlorosuccinates with specified amines.

SUMMARY OF THE INVENTION

Although other routes exist for the preparation of anilinofumarates in order to prepare quinoline-2,3-dicarboxylic acids for producing the herbicidal agents 2-(4-isopropyl-4-methyl-5-oxo-2-imidazolin-2-yl)quinoline-3-carboxylic acids, esters and salts thereof, the present invention relates to a process for the preparation of quinoline-2,3-dicarboxylic acid with the use of aniline and maleic anhydride to obtain a ready source of acridine.

It is an object of the present invention, therefore, to provide a ready source of starting materials to form quinoline-2,3-dicarboxylic acid. This objective is fulfilled by reacting an oxidized anilinosuccimide with a maleic anhydride, cyclizing the resulting reactant to result in an acridinimide and hydrolyzing the acridinimide to obtain the quinoline-2,3-dicarboxylic acids.

These and other objects of the invention will become more apparent by the detailed description of the invention provided hereinbelow.

DETAILED DESCRIPTION OF THE INVENTION

The present invention relates to a novel method for the preparation of quinoline-2,3-dicarboxylic acid, said method comprising oxidizing an N-substituted-3-anilinosuccinimide of formula I

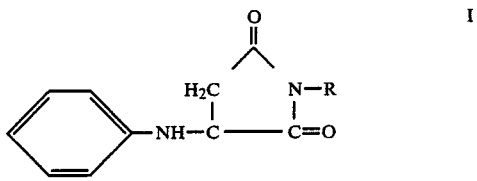

wherein R is phenyl or $C_1$–$C_6$ alkyl in an inert solvent; reacting the thus-formed formula II 3-anilino-N-substituted-maleimide

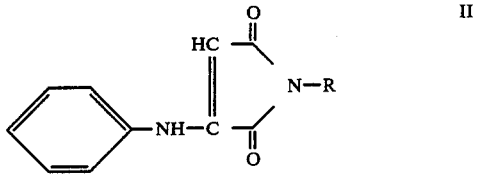

wherein R is as defined hereinabove with a minimum of 2 molar equivalents (2 molar equivalents or greater) of dimethylformamide dimethyl acetal in an inert hydrocarbon aromatic hydrocarbon, chlorinated hydrocarbon or chlorinated aromatic hydrocarbon solvent, or with one molar equivalent of a Vilsmeier reagent prepared from dimethylformamide and two molar equivalents of $POCl_3$ in dichloromethane at reflux; isolating the resulting formula III 3-phenylimino-4-dimethylaminomethylene-N-substituted-succinimide

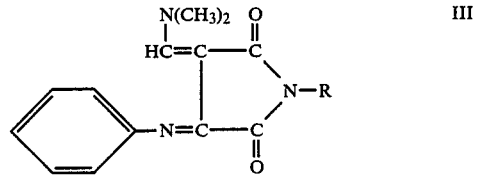

wherein R is as defined hereinabove; cyclizing the formula III compound by treatment with polyphosphoric acid at 130° C. to 145° C. to yield formula IV substituted-acridinimide

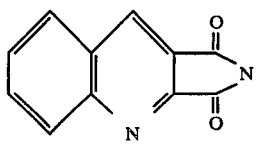

wherein R is as defined hereinabove; hydrolyzing the formula IV acridinimide with a minimum one (1) molar equivalent base (one molar equivalent or greater) in a solvent of water or an aqueous alcohol; cooling the reaction mixture; isolating the thus formed quinoline-2,3-dicarboxylic, formula V

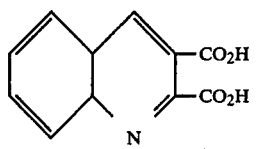

acid by acidification of said cooled reaction mixture; and collecting the precipitated product.

It has been found that the reaction of formula II 3-anilino-N-substituted-maleimides compounds readily prepared by oxidation of formula I N-substituted-3-anilinosuccinimide with oxidizing agents such as $MnO_2$ or chloranil, in an inert solvent at a temperature of about 25° C. to 150° C., with one molar equivalent of a Vilsmeir reagent prepared from dimethyl formamide and $POCl_3$ in refluxing methylene chloride, or preferably with a minimum of two molar equivalents of dimethylformamide dimethyl acetal in solvents such as toluene, xylene, benzene, methylene chloride, ethylene chloride, chlorobenzene at a temperature of about 25° C. to 140° C. yields formula IV compounds. These formula IV compounds are easily cyclized to formula IV acridinimides when treated with polyphosphoric acid at a temperature of about 130° C. to 145° C.

Additionally, it has been found that the formula IV acridinimides are readily hydrolysed in water or aqueous-alcoholic solvent systems with a minimum of two molar equivalents of base (2 molar equivalents or greater). Preferable bases are sodium hydroxide, potassium hydroxide, or mixtures thereof at concentrations of 5% to 50%, on a weight basis, giving quinoline-2,3-dicarboxylic acid as its salt. This is then isolated as the free acid by acidification of the cooled reaction mixture and collection of the precipitated product.

Advantageously, the above method provides a novel route to quinoline-2,3-dicarboxylic acid utilizing formula I 3-anilinosuccinimides which may be prepared in high yields from maleic anhydride, a ready source of starting material available in large quantities, by known procedures, such as those described by S. I. Burmistrov. et al., *J. Org. Chem. U.S.S.R.*, 8: 1102 (1972), and L. E. Coleman, Jr. et al., *J. Org. Chem.*, 24: 135 (1959) (incorporated herein by reference).

The present invention is further illustrated by the following which are provided as illustrations of the invention and not limitations thereof.

EXAMPLE 1

Preparation of 3-anilino-N-phenylsuccinimide

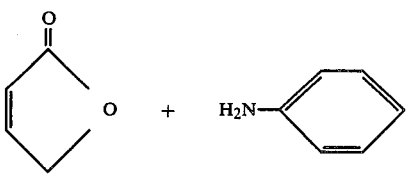

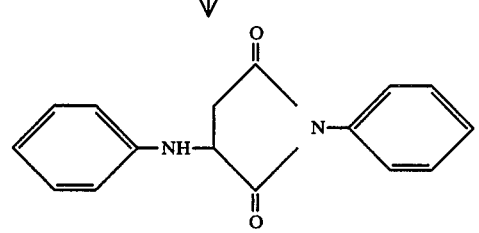

A mixture of 9.8 g (0.1 mol) of maleic anhydride, 18.6 g (0.20 mol) of aniline and 75 mL of o-dichlorobenzene is heated while stirring at 175°-180° C. for one hour. At 175° C. all of the solid goes into solution. A Dean Stark trap is used to collect the condensate during the reaction. Cooling gives a thick precipitate, which is stirred in 50 mL of ethanol, cooled in ice and collected by filtration to give 16.6 g of the product having m.p. 211°-214.5° C. Concentration of the filtrate and slurrying in 50 mL of ethanol gives another 3.0 g of product, giving a total yield of 74%.

EXAMPLE 2

Preparation of 3-anilino-N-butylsuccinimide

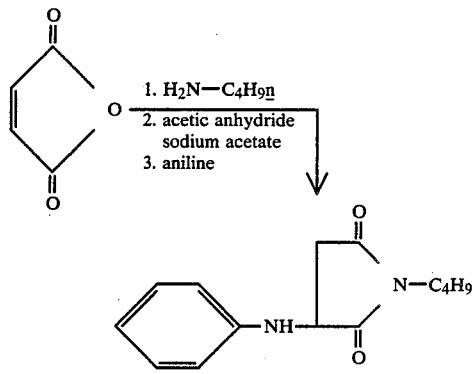

Maleic anhydride is reacted with n-butylamine under the conditions reported by L. E. Coleman et al., in *J. Org. Chem.*, 24: 135, (1959). A mixture containing the thus-formed n-butylmaleamic acid (12.0 g, 0.07 mol), anhydrous sodium acetate (2.7 g) and acetic anhydride (29 mL) is heated at 85° C. to 90° C. for 30 minutes. The solution is cooled to 40° C. and poured into 55 mL of water. The layers are stirred at room temperature for 15 minutes, the diluted to 275 mL. A dark oil precipitates. Extraction with 100 mL of $CH_2Cl_2$, then another 25 mL of $CH_2Cl_2$, and evaporation of solvent gives 9.9 g of n-butylmaleimide as an oil, ir, 1735 (sh) and 1700 cm−1. A solution of 9.9 g (0.065 mol) of the n-butylmaleimide and 35 mL of acetic acid is treated with 6.51 g (0.07 mol) of aniline, with the resulting solution heated at 120° C. for 30 minutes. The solution is cooled and poured into 280 mL of water. The amorphous material is collected and recrystallized from isopropyl alcohol to give 9.3 g of n-butyl anilinosuccinimide as off-white crystals, m.p. 97°–100° C., ir, 3350, 1720 (sh), 1680, 1600 cm−1; mass spec, (ci) m/e 247. Anal. Calcd. for C14H18N2O2: C, 68.29; H, 7.32; N, 11.38. Found: C, 68.46; H, 7.28; N, 11.25.

EXAMPLE 3

Preparation of 3-anilino-N-phenylmaleimide

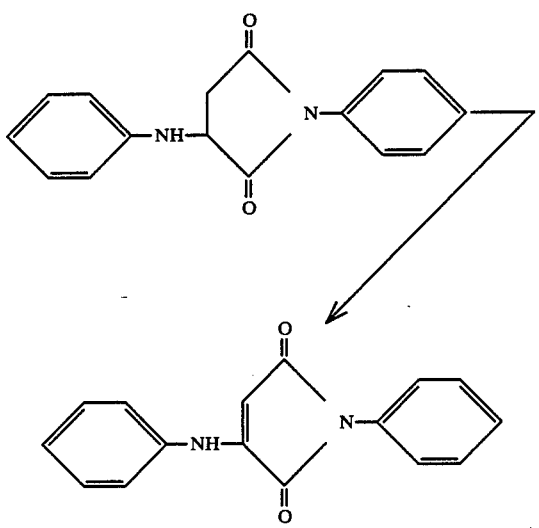

A. A mixture of 1.98 g (7.5 mmol) of the anilinosuccinimide prepared in Example 1 above and 1.96 g (22.5 mmol) of MnO2 in 45 mL of toluene is refluxed for six hours. The mixture is filtered, while hot, and the resulting solid is heated in another 50 mL of boiling toluene and filtered again while hot. Cooling the combined toluene filtrates gives 450 mg of the title product as yellow-orange needles. Concentration of the toluene solution gives another 360 mg; m.p. 228°–233° C. (lit (7) m.p. 230°–230.5° C.).

B. A mixture of 1.32 g (5.0 mmol) of the anilinosuccinimide 1.22 g (5.0 mmol) of chloranil and 30 mL of xylene are refluxed for four hours. The mixture is cooled to room temperature and the precipitate collected and recrystallized from acetonitrile to give 0.86 g (65%); m.p. 233°–235° C.

Utilizing the procedure above and substituting N-butylanilinosuccinimide for the 3-amino-N-phenylsuccinimide yields 93% of N-butylanilinomaleimide which upon crystallization from isopropyl alcohol has a m.p. of 128°–130° C. Anal. Calcd. for C14H16N2O2: 68.85; H, 6.56; N, 11.48. Found: C, 68.58; H, 6.45; N, 11.38.

EXAMPLE 4

Preparation of 3-phenylimino-4-dimethylaminomethylene-N-phenylsuccinimide

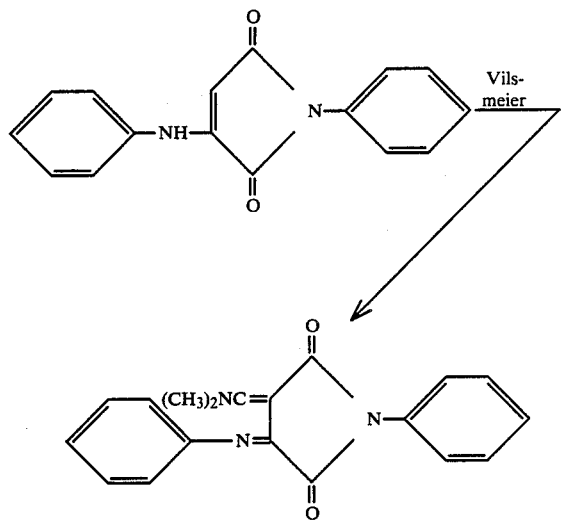

A. A solution of 13.2 g (0.05 mol) of the anilinomaleimide prepared in Example 3, 11.9 g (0.10 mol) of dimethylformamide dimethyl acetal and 250 mL of toluene is refluxed for three hours. Cooling the solution gives a dark maroon solid which is stirred in 200 mL of hot ethanol and collected to give the title product 12.3 g (77%) having m.p. 196°–200.5° C. Recrystallization from acetonitrile gives brown-gold crystals, mp 199.5°–201.5° C. (dec).

Anal. Calcd. for C19H17N3O2: C, 71.47; H, 5.33; N, 13.17. Found: C, 71.42; H, 5.56; N, 12.98.

B. To a solution of 0.37 g (5. mmol) of DMF and 15 mL of methylene chloride is added dropwise, with cooling (15° C.–20° C.), 1.68 g (11 mmol) of POCl3. The slurry is stirred at room temperature for 30 minutes, and the anilinomaleimide is added as a solid. The mixture is refluxed for three hours, and a dark maroon solution forms. The solution is cooled in ice, and 20 mL of methylene chloride and 10 mL of water are added. Aqueous Na2CO3 is added until the aqueous phase is alkaline, and the two layers are stirred for 15 minutes and filtered. The organic phase is separated and evaporated to give a viscous oil, which is dissolved in 40 mL of ethanol. Cooling gives 200 mg of the title product as an orange solid, m.p. 189°–195° C. Evaporation of solvent and recrystallization from ethyl acetate gives another 200 mg.

When the Vilsmeier reaction using DMF is attempted in refluxing monochlorobenzene, toluene or ethylene chloride, only polymeric material is obtained.

Utilizing procedure A above and substituting the N-butylanilinomaleide for 3-anilino-N-phenylmaleimide yields the corresponding 3-phenylimino-4-dimethylaminomethylene-N-butylsuccinimide.

EXAMPLE 5

Preparation of N-phenylacridinimide

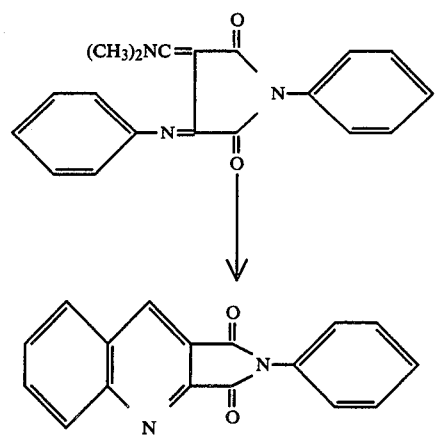

A solution of 2.0 g of the N-phenylsuccinimide, prepared as in Example 4, in 60 g of polyphosphoric acid, is heated at 140° C.–145° C., with occasional stirring, for 20 minutes. The red maroon solution is cooled and poured into 400 g of ice and water. The crude product is collected, stirred in 100 mL of hot ethanol and isolated as an off-white solid, weighing 1.54 g (90%) having a m.p. 315°–321° C.

Utilizing the above procedure substituting the N-butylsuccinimide prepared in Example 4 for the N-phenylsuccinimide yields N-butylacridinimide in 47% yield, which upon crystallization has m.p. 165°–167° C. Anal. Calcd. for $C_{15}H_{14}N_2O_2$: C, 70.87; H, 5.51; N, 11.02. Found C, 70.78; N, 5.41; N, 10.96.

EXAMPLE 6

Preparation of Quinoline-2,3-dicarboxylic acid

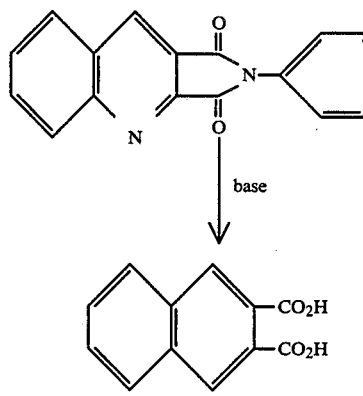

A mixture of 274 mg (1.0 mmol) of N-phenylacridinimide, 160 mg (4.0 mmol) of NaOH in 1.5 mL of water and 10 mL of ethanol is heated at reflux for three hours. Water (10 mL) is added, while the ethanol is removed by distillation, and the resulting solution is then heated at reflux for two hours. The solution is cooled in an ice bath and conc HCl is added, dropwise, until the mixture is acidic. The thick mixture is filtered, washed with water and dried in a vacuum oven at 60° C. to give 179 mg of the product with m.p. 279° C.–281° C. (dec with loss of $CO_2$ at 105° C.–120° C.).

What is claimed is:

1. A method for the preparation of quinoline-2,3-dicarboxylic acid, said method comprising: oxidizing with an oxidizing agent in an inert solvent an N-substituted-3-anilinosuccinimide of formula I

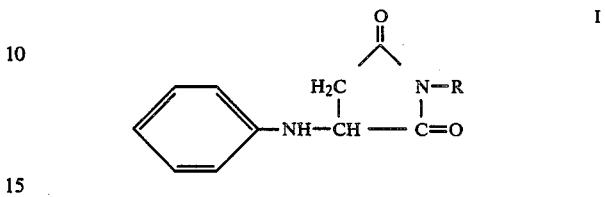

wherein R is phenyl or $C_1$–$C_6$ alkyl; reacting the thus formed formula II 3-anilino-N-substituted-maleimide

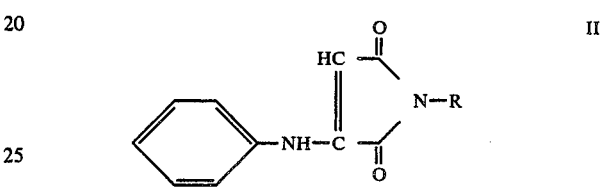

wherein R is as defined hereinabove with a minimum of 2 molar equivalents of dimethylformamide dimethylacetal in an inert hydrocarbon aromatic hydrocarbon, chlorinated hydrocarbon or chlorinated aromatic hydrocarbon solvent, or one molar equivalent of a Vilsmeier reagent prepared from dimethylformamide and two molar equivalents of $POCl_3$ in dichloromethane at reflux; isolating the resulting formula III 3-phenylimino-4-dimethylaminomethylene-N-substituted-succinimide

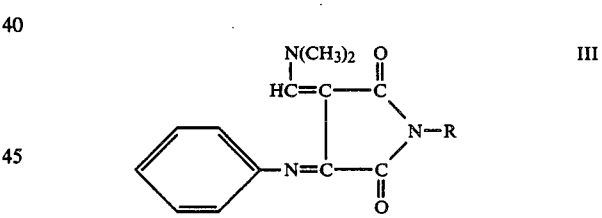

wherein R is as defined hereinabove; cyclizing the formula III compound by treatment with polyphosphoric acid at 130° C. to 145° C. to yield a formula IV substituted-acridinimide

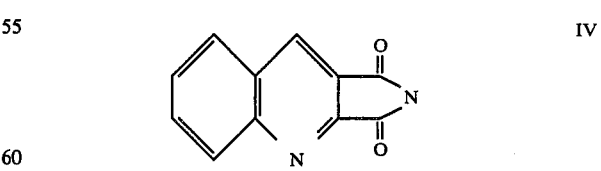

wherein R is as defined hereinabove; hydrolyzing the formula IV acridinimide with a minimum one molar equivalent base in a solvent of water or an aqueous alcohol; cooling the reaction mixture; isolating the thus formed quinoline-2,3-dicarboxylic acid (formula V) by acidification of the cooled reaction mixture;

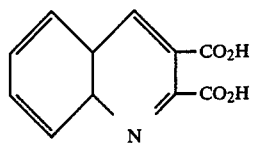

and collecting the precipitated product.

2. A method according to claim 1, wherein said formula II 3-anilino-N-substituted maleimide is reacted with a minimum of two molar equivalents of dimethylformamide dimethyl acetal, in an inert solvent, at a temperature of about 25° C. to 140° C.

3. A method according to claim 2, wherein said solvent is toluene, benzene, xylene, methylene chloride, ethylene chloride, chlorobenzene, or mixtures thereof.

4. A method according to claim 3, wherein said oxidizing agent is $MnO_2$ or chloranil; and said inert solvent is toluene or xylene at reflux.

5. A method according to claim 4, wherein said base to hydrolyze said formula IV N-substituted-acridinimide is aqueous or aqueous alcoholic sodium hydroxide, potassium hydroxide, or mixtures thereof, at a concentration of about 5% to 50%, on a weight basis.

6. A method according to claim 5, wherein said base used is two or more molar equivalents.

7. A method according to claim 6, wherein said formula IV N-substituted-acridininde is hydrolyzed at reflux for about two to six hours.

* * * * *